United States Patent
Botha et al.

(10) Patent No.: US 6,586,649 B1
(45) Date of Patent: Jul. 1, 2003

(54) PRODUCTION OF PROPYLENE

(75) Inventors: Jan Mattheus Botha, Sasolburg (ZA); Muzikayise Mthokozisi Justice Mbatha, Zamdela (ZA); Bongani Simon Nkosi, Sasolburg (ZA); Alta Spamer, Vanderoijlpark (ZA); Joan Swart, Vaalpark (ZA)

(73) Assignee: Sasol Technology (Proprietary) Limited, Sasolburg (ZA)

( * ) Notice: Subject to any disclaimer, the term of this patent is extended or adjusted under 35 U.S.C. 154(b) by 0 days.

(21) Appl. No.: 09/763,504

(22) PCT Filed: Aug. 9, 1999

(86) PCT No.: PCT/IB99/01407
§ 371 (c)(1),
(2), (4) Date: Jul. 12, 2001

(87) PCT Pub. No.: WO00/14038
PCT Pub. Date: Mar. 16, 2000

(30) Foreign Application Priority Data

Sep. 4, 1998 (ZA) .............................................. 98/8113

(51) Int. Cl.⁷ ................................................ C07C 6/04
(52) U.S. Cl. ....................................... 585/646; 585/647
(58) Field of Search .................................. 585/646, 647

(56) References Cited

U.S. PATENT DOCUMENTS

| | | | | |
|---|---|---|---|---|
| 3,872,180 A | * | 3/1975 | Nakatomi et al. | 502/306 |
| 4,041,095 A | * | 8/1977 | Kuo | 208/120.01 |
| 4,255,284 A | * | 3/1981 | Hardman | 502/211 |
| 5,300,718 A | * | 4/1994 | McCaulley | 585/324 |

FOREIGN PATENT DOCUMENTS

| | | |
|---|---|---|
| CA | 2215426 | 3/1998 |
| EP | 0832867 | 4/1998 |

* cited by examiner

*Primary Examiner*—Thuan D. Dang
(74) *Attorney, Agent, or Firm*—Ladas & Parry

(57) ABSTRACT

The invention provides a process for the production of propylene by butene metathesis. The process includes contacting a feedstock, which contains butene selected from 1-butene, 2-butene and mixtures thereof, with a catalyst which includes a catalytic amount of at least one metal oxide selected from oxides of the transition metals. The contacting is under reaction conditions which include a temperature of 300–600 øC. and a pressure of 1 20 atmospheres, and converts the butene to propylene, thereby to produce a reaction product containing propylene. $C_5$— and higher hydrocarbons produced by the metathesis are separated from the reaction product and are recycled to the reaction where they are contacted with the catalyst.

17 Claims, No Drawings

PRODUCTION OF PROPYLENE

THIS INVENTION relates, broadly, to the production of propylene. More particularly, the invention relates to a process for the production of propylene, suitable for producing propylene from both pure and mixed hydrocarbon feedstocks.

From EP-A-O832867 a process for producing propylene is known.

According to the invention, broadly, there is provided a process for the production of propylene by butene metathesis which comprises contacting a feedstock, which contains butene selected from the group consisting of 1-butene, 2-butene and mixtures thereof, with a catalyst which includes a catalytic amount of at least one metal oxide selected from the group consisting of the oxides of the transition metals, under reaction conditions which include a temperature of 300–600° C. and a pressure of 1–20 atmospheres, to convert the butene to propylene, thereby to produce a reaction product containing propylene.

In this specification any reference to 1-butene or 2-butene includes all the isomers thereof.

Conveniently, the temperature is 500–600° C., eg about 550° C. and the pressure may be about 1 atmosphere.

While the butene (which can also be referred to as butylene) may be in the form of a relatively pure butene feedstock, containing substantially only butene, it may instead form part of a mixed feedstock including, in addition to the butene, a plurality of other hydrocarbons. Thus, the feedstock may be a mixed hydrocarbon feedstock including, in addition to said butene, a plurality of other hydrocarbons.

In the latter case the feedstock may be a condensate, being for example a Fisher-Tropsch process-derived feedstock which is a condensate derived by reacting a synthesis gas mixture including carbon monoxide and hydrogen, in a selected $CD:H_2$ ratio, over a Fisher-Tropsch catalyst which may be a cobalt-based catalyst, an iron-based catalyst, a catalyst based on both iron and cobalt, or a mixture of such catalyst. The feedstock or condensate derived from the Fisher-Tropsch process will typically not be subjected to cracking at any stage, and it may include, in addition to butenes such as the isomers 1-butene and 2-butene, one or more other alkenes or olefins, such as ethylene, propylene and various pentenes, hexanes and $C_7$- or higher alkenes. In particular, the feedstock may be produced by a Fisher-Tropsch reaction at a temperature of 280–370° C., preferably 300–340° C., eg 320° C., in a circulating fluidized-bed reactor or in a fixed-bed reactor, or in a fixed fluidised bed reactor at a pressure of 10–40 atmospheres (1 013 250–4 053 000 $N/m^2$), preferably 15–25 atmosphere (1 519 875–2 533 125 $N/m^2$), eg 20 atmospheres (2 026 500 $N/m^2$), to produce a hydrocarbon product containing a range of hydrocarbon compounds with carbon numbers of $C_1$–$C_{38}$ or more, including olefinic hydrocarbon compounds.

In other words, more specifically, the feedstock may be a Fisher-Tropsch process-derived feedstock condensate derived by passing a synthesis gas mixture including carbon monoxide and hydrogen over a Fisher-Tropsch catalyst, the catalyst being selected from the group consisting of cobalt-based catalysts, iron-based catalysts, catalysts based on both iron and cobalt, and mixtures thereof; and the feedstock preferably contains, in addition to said butene, another alkene selected from the group consisting of ethylene, propylene, pentene, hexene, heptene, alkenes with more than 7 carbon atoms, and mixtures thereof. In this regard, the references to pentene, hexene, heptene and alkenes with more than 7 carbon atoms are references to all the isomers thereof. Preferably, the feedstock is a condensate derived from a high temperature Fisher-Tropsch process having a reaction temperature of 280–370° C. and a reaction pressure of 10–40 atmospheres (1 013 250–4 053 000 $N/m^2$), hydrocarbon compounds of the feedstock including, in addition to olefinic hydrocarbons, also methane and other hydrocarbons, at least some of the hydrocarbons having carbon numbers higher than 35.

When a Fischer-Tropsch-derived feedstock is used as described above, it may be fractionated prior to the contacting thereof with the transition metal oxide catalyst, to obtain a fraction, for use as the feedstock in the reaction, containing an increased proportion of desired alkenes. The fractionation may be by distillation, for example so-called short path distillation at a temperature of 150–400° C. and at a pressure of 0.02–2.0 atmospheres$\times 10^{-3}$ (2.0265–202.65 $N/m^2$), preferably 200–350° C. and 0.07–1.5 atmospheres$\times 10^{-3}$ (7.09276–151.9875 $N/m^2$), to obtain a fractionated feedstock having various proportions of $C_2$ olefins, $C_3$ olefins, α-olefins, branched olefins and a small proportion of internal olefins, the fractionated feedstock being used for the production of propylene according to the present invention. In particular, the feedstock may be an uncracked feedstock which has been subjected to fractionation to increase the proportion of olefins therein.

Instead, a feedstock may be used which is a condensate stream from a naphtha cracking process or from a gas cracking process, including streams of Raffinate I, Raffinate II and/or Raffinate III.

By Raffinate I is meant the residue which is obtained when a $C_4$ stream from a naphtha cracking process or from a gas cracking process (the $C_4$ stream typically containing, as its chief components, n-butene, 1-butene, 2-butene, isobutene and 1,3-butadiene, and optionally some isobutane and said chief components together forming up to 99% or more of the $C_4$ stream) is subjected to the removal of 1,3-butadiene therefrom. Thus removal may be by extractive distillation with an aprotic solvent such as acetonitrile, N-methylpyrrolidone or N,N-dimethylformamide, any remaining butadiene optionally being removed from the residue by an after-treatment such as selective hydrogenation, the residue being Raffinate I and containing, in substance, 1-butene, 2-butene and isobutene.

By Raffinate II in turn is meant a mixture of 1-butene and 2-butene which remains when Raffinate I has the isobutene separated therefrom by hydrogenation to tert-butanol in the presence of sulphuric acid; by reaction of the Raffinate I with methanol to synthesize methyl tert-butyl ether; or by oligomerization or polymerization of the isobutene.

Raffinate III in turn is meant what is obtained when the 1-butene in Raffinate II is separated therefrom by fractionation, extractive distillation or molecular sieve absorption, the residue of cis 2-butene and trans 2-butene remaining being Raffinate III. Raffinates I, II and III are described in more detail in Industrial Organic Chemicals, by Harold A. Wittcoff and Bryan G. Reuben, a Wiley Interscience Publication, published by John Wiley & Sons. Inc., New York, N.Y., U.S.A. (1996).

Another feedstock which may be used in a product obtained from dehydrogenation of paraffins, i.e. from dehydrogenation of alkanes, to yield olefins, i.e. alkenes, such products containing butenes, pentenes and higher olefins. Accordingly, the feedstock may be selected from Raffinate I, Raffinate II, Raffinate III and mixtures thereof; or it may be a product derived from the dehydrogenation of alkanes.

It is a feature of the invention that products are formed which are predominantly in the $C_2$–$C_8$ product range, with a propylene:ethylene mass ratio of up to 3:1, depending on the process conditions and catalyst used. The invention has been found to be capable of producing more propylene than ethylene from either a feedstock which consists of pure $C_4$ olefins (butenes), for example $C_4$ α-olefins, or from a feedstock which is a condensate stream which includes such $C_4$ olefins.

The transition metal oxide catalyst used for the catalytic conversion of butene to propylene is preferably selected from oxides of molybdenum, or of rhenium or of tungsten, or of mixtures of any two or more of tungsten, rhenium and molybdenium. This catalyst may be a homogeneous (unsupported) catalyst or a heterogeneous (supported) catalyst. Conveniently the catalyst is supported and any convenient support may be used, provided it neither interferes with nor inhibits the production of propylene from butene according to the invention. Suitable supports include those based on or including ceramic supports such as silica, alumina, titania, zirconia or mixtures thereof, with silica being preferred. The catalyst can be attached to its support in any convenient fashion, such as those known in the art, in particular by sublimation or by wet impregnation. The transition metal oxide constituent of the catalyst may amounts to 1–30% by mass of the total catalyst mass (transition metal and support together), preferably 6–20% thereof. If desired, the catalyst mass may include one or more promoters such as phosphates, borates or magnesium oxide, which increase selectivity towards propylene. Instead, the catalyst mass may include one or more promoters which are alkali metals, such as lithium, sodium, potassium and cesium, which decrease selectivity towards propylene. In particular the catalyst may be a $WO_3$-based (tungsten oxide-based) catalyst containing Cs (cesium) as a promoter.

In other words, the transition metal oxide catalyst used for the conversion of butene to propylene may be selected from the group consisting of the oxides of molybdenum, the oxides of rhenium, the oxides of tungsten, and mixtures thereof; and the transition metal oxide catalyst for the conversion of butene to propylene may form part of a catalyst mass in which the transition metal oxide is supported on a solid ceramic support of a material selected from the group consisting of silica, alumina, titania, zirconia and mixtures thereof. In this case the transition metal oxide may form 1–30% by mass of the total heterogeneous catalyst mass. In particular, the catalyst of the heterogeneous catalyst mass may consist essentially of tungsten oxide, being supported on silica, the catalyst mass containing a promotor selected from the group consisting of cesium (to decrease selectivity towards propylene) and phosphates (to increase selectivity towards propylene).

Preferably the catalyst has as high a proportion of acid sites thereon as practicable. Thus, tests conducted by the Applicant have shown that carrying out the process of the present invention with a catalyst having a relatively high proportion of acid sites favours the production, from butene, of propylene (and pentenes) over ethylene (and hexanes). Acidity of the catalyst can be enhanced by treating the catalyst with organic acids or inorganic acids, or by impregnation thereof with cations such as those of phosphates or borates. Acidity of the catalyst can, conversely, be reduced by blocking acid sites thereon, by means of alkaline earth metals, the presence of which alkaline earth metals can improve the selectivity of the reaction in favour of ethylene and hexenes.

The reaction product may be separated into its constituent parts by conventional separation techniques, for example into an ethylene-containing fraction, a propylene-containing fraction, a $C_4$-containing fraction and a fraction including $C_5$- and higher hydrocarbons, with the $C_4$ fraction optionally being recycled to the reaction. Thus, unreacted butene may be separated from the reaction product, the separated unreacted butene being converted to propylene by recycling it and contacting it, together with the feedstock, with the transition metal oxide catalyst; and $C_5$- and higher hydrocarbons may be separated from the reaction product, the separated $C_5$- and higher hydrocarbons then being converted to propylene by recycling them and contacting them, together with the feedstock, with the transition metal oxide catalyst. This recycling can act to increase the yield of propylene. The invention has been shown to be capable, from a pure 1-butene feedstock, of obtaining a product having a product spectrum as set forth in the following table, Table 1:

TABLE 1

| Constituent | % by Mass |
| --- | --- |
| ethylene fraction | 8 |
| propylene fraction | 35 |
| $C_4$ fraction | 20 |
| $C_5$-and higher fraction | 27 |

The invention will now be described, by way of non-limiting illustration, with reference to the following illustrative Examples:

EXAMPLES

In general, all experimental runs made and involved in the Examples were made by passing pure 1-butene or a 1-butene-containing Fischer-Tropsch process-derived condensate, of a $C_4$ fraction of a Raffinate I stream or a $C_4$ fraction of a Raffinate II stream, downwards at a reaction pressure of 1 atmosphere through a vertical pipe reactor, unless otherwise specified, an exception being Example 3 in which a mixture of 1-butene and 2-butene was used. The reactor contained a fixed bed of catalyst and was about 25.4 mm in inside diameter and 400 mm in length, being located in a temperature-controlled furnace and having a thermocouple positioned in its catalyst bed.

A 100 mm depth of 2 mm diameter glass beads was held in the lower end of the pipe, supported therein by a layer of quartz wool under the beads. Another layer of quartz wool on top of the beads acted as a support for the catalyst bed, which comprised about 12 g of the catalyst. A further layer of quartz wool was placed on top of the catalyst and the pipe was, above this uppermost layer of glass wool, filled up to the top with further 2 mm diameter glass beads. Each catalyst was activated by heating it to 550° C. for 12 hours with a stream of air flowing down through the pipe, followed by heating at 600° C. under a downward flow of nitrogen flow for 2 hours, the catalyst then being cooled under said nitrogen flow to the actual reaction temperature used for the propylene synthesis, which was typically 550° C. Catalysts were prepared by methods known in the art.

EXAMPLE 1

Two catalysts were used, in the form of $WO_3$ supported on silica, the silica having an average particle size of 300 µm. The catalysts respectively comprised $WO_3$ and silica in $WO_3$:silica mass ratios of 8:92 and 20:80. These catalysts were respectively tested at temperatures of 500–550° C. using a feedstock of pure 1-butene at a gas hourly space velocity (GHSV) of 500 h$^{-1}$. Samples were taken after the reaction had been on line for 4 hours. Results are set forth in the following table, Table 2:

TABLE 2

|  | $WO_3.SiO_2$ Catalyst (8% m/m $WO_3$) | $WO_3.SiO_2$ Catalyst (20% m/m $WO_3$) |
| --- | --- | --- |
| Temperature (°C.) | 500 | 550 | 550 |
| $C_4$-Conversion (%) | 75.8 | 84.5 | 91.8 |
| 2-Butene Yield (%) | 22.5 | 20.9 | 11.2 |
| Ethylene Yield (%) | 5.4 | 5.6 | 4.3 |
| Propylene Yield (%) | 19.3 | 31.7 | 18.3 |
| $C_5$ and Higher Yield (%) | 28.6 | 26.3 | 58 |

EXAMPLE 2

Two catalysts were also used in this Example, also in the form of $WO_3$ supported on $SiO_2$, each comprising $WO_3$ and $SiO_2$ in a $WO_3$:$SiO_2$ mass ratio of 8:90. One of the catalysts contained 2% by mass $Cs^+$ cations and the other contained 2% by mass $PO_4^{3-}$ anions. These catalysts were tested at 550° C. and at a GHSV of 1000 h$^{-1}$ using a pure 1-butene feedstock and results are set forth in the following table, Table 3:

TABLE 3

|  | $WO_3.SiO_2$ Catalyst (2% Cs and 8% $WO_3$ m/m) | $WO_3.SiO_2$ Catalyst (2% $PO_4$ and 8% $WO_3$ m/m) |
| --- | --- | --- |
| $C_4$-Conversion (%) | 50 | 87.5 |
| 2-Butene Yield (%) | 2.7 | 18.5 |
| Ethylene Yield (%) | 8.7 | 5.4 |
| Propylene Yield (%) | 10.1 | 32.8 |
| $C_5$ and Higher Yield (%) | 28.5 | 30.8 |

EXAMPLE 3

In this Example a catalyst in the form of a $WO_3$ supported on $SiO_2$ was used, in which the $WO_3$ and $SiO_2$ were in a mass ratio of 8:92. The process was operated at 550° C. and the GHSV was 500 h$^{-1}$. As a feedstock was used a mixture of 1-butene and 2butene (containing both the cis- and trans isomers) in a 1-butene:2-butene mass ratio of 1:9. Results are set forth in the following table, Table 4:

TABLE 4

|  | $WO_3.SiO_2$ Catalyst (8% $WO_3$ m/m) |
| --- | --- |
| $C_4$-Conversion (%) | 54 |
| Ethylene Selectivity (%) | 5.6 |
| Propylene Selectivity (%) | 50 |
| $C_5$ and Higher selectivity (%) | 44.4 |

EXAMPLE 4

In this Example the same catalyst was used as in Example 3, the process being operated at 550° C. with an overall GHSV of 2900 h$^{-1}$. The 1-butene feedstock was fed through the reactor at a GHSV of 1000$^{-1}$. Some unreacted butene was recycled, together with most of the $C_5$–$C_9$ hydrocarbon fraction formed in the reactor, to achieve the overall GHSV of 2900 h$^{-1}$, the balance thereof being purged to maintain the overall GHSV constant at 2900 h$^{-1}$. Results are set forth in the following table, Table 5.

TABLE 5

|  | $WO_3.SiO_2$ Catalyst (8% $WO_3$ m/m) |
| --- | --- |
| $C_4$-Conversion (%) | 60.9 |
| Ethylene Selectivity (%) | 7.3 |
| Propylene Selectivity (%) | 46.5 |
| $C_4$–$C_{14}$ Purge (% - based on 1-butene feed taken in) | 19.7 |

Ways in which propylene can be produced by metathesis of butenes are limited. The Applicant is aware that 2-butene (both the cis- and trans isomers) can be metathesized with ethylene from a separate feed to yield propylene. An advantage of the present invention, however, is that it does not require a separate ethylene feed in order to produce propylene by metathesis of butene. The process of the present invention can be manipulated, by changing the acid/base properties of the catalyst, as illustrated in Examples 1 and 2, which in turn changes the selectivity of the process as regards ethylene and propylene. Furthermore, it has been found that that constant activity of the transition metal oxide catalyst can be maintained, at the high temperatures employed in the Examples, for periods of up to 48 hours or more, whereas at lower temperatures catalyst activity is lost within a few hours.

What is claimed is:

1. A process for the production of propylene by butene metathesis which includes contacting a feedstock, which contains butene selected from the group consisting of 1-butene, 2-butene and mixtures thereof wherein the butene in the feedstock consists essentially of the butene selected from the group, with a catalyst which includes a catalytic amount of at least one metal oxide selected from the group consisting of the oxides of the transition metals, under reaction conditions which include a temperature of 300–600° C. and a pressure of 1–20 atmospheres, to convert the butene to propylene, thereby to produce a reaction product containing a propylene fraction and, additional thereto, an ethylene fraction, a $C_4$ fraction and a $C_5$— and higher fraction, the propylene fraction being present in the reaction product in a higher proportion in terms of mass percentage than any one of said additional fractions, the process further including separating $C_5$— and higher hydrocarbons produced by the butene methathesis from the reaction product and then converting the separated $C_5$— and higher hydrocarbons to propylene by recycling them and contacting them, together with the feedstock, with the transition metal oxide catalyst.

2. A process as claimed in claim 1, in which the feedstock is a mixed hydrocarbon feedstock including, in addition to said butene, a plurality of other hydrocarbons.

3. A process as claimed in claim 2, in which the feedstock is a Fisher-Tropsch process-derived condensate derived by passing a synthesis gas mixture including carbon monoxide and hydrogen over a Fisher-Tropsch catalyst, the catalyst being selected from the group consisting of cobalt-based catalysts, iron-based catalysts, catalysts based on both iron and cobalt, and mixtures thereof.

4. A process as claimed in claim 3, in which the feedstock contains, in addition to said butene, another alkene selected from the group consisting of ethylene, propylene, pentene, hexane, heptene, alkenes with more than 7 carbon atoms, and mixtures thereof.

5. A process as claimed in claim 4, in which the feedstock is a condensate derived from a high temperature Fischer-Tropsch process having a reaction temperature of 280–370 øC. and a reaction pressure of 10–40 atmospheres, hydrocarbon compounds of the feedstock including, in addition to olefinic hydrocarbons, at least some of the hydrocarbons having carbon numbers higher than 35.

6. A process as claimed in claim 4 inclusive, in which the feedstock is an uncracked feedstock which has been subjected to fractionation to increase the proportion of olefins therein.

7. A process as claimed in claim 1, in which the feedstock is selected from Raffinate I, Raffinate II, Raffinate III and mixtures thereof.

8. A process as claimed in claim 1, in which the feedstock is a product derived from the dehydrogenation of alkanes.

9. A process as claimed in claim 1, in which the transition metal oxide catalyst used for the conversion of butene to propylene is selected from the group consisting of the oxides of molybdenum, the oxides of rhenium, the oxides of tungsten, and mixtures thereof.

10. A process as claimed in claim 1, in which the transition metal oxide catalyst used for the conversion of butene to propylene forms part of a heterogeneous catalyst mass, in which the transition metal oxide is supported on a solid ceramic support of a material selected from the group consisting of silica, alumina, titania, zirconia and mixtures thereof.

11. A process as claimed in claim 10, in which the transition metal oxide forms 1–30% by mass of the total heterogeneous catalyst mass.

12. A process as claimed in claim 11, in which the catalyst of the heterogeneous catalyst mass consists essentially of tungsten oxide, and is supported on silica, the catalyst mass containing a promotor selected from the group consisting of cesium and phosphates.

13. A process as claimed in claim 1, in which unreacted butene is separated from the reaction product, the separated unreacted butene then being converted to propylene by recycling it and contacting it, together with the feedstock, with the transition metal oxide catalyst.

14. A process for the production of propylene by butene metathesis which includes contacting a feedstock, which contains butene selected from the group consisting of 1-butene, 2-butene and mixtures thereof, with a catalyst which includes a catalytic amount of at least one metal oxide selected from the group consisting of the oxides of the transition metals, under reaction conditions which include a temperature of 500–600° C. and a pressure of 1–20 atmospheres, to convert the butene to a reaction product comprising a propylene fraction and, additional thereto, an ethylene fraction, a $C_4$ fraction and a $C_5$— and higher fraction, the propylene fraction being present in the reaction product in a higher proportion in terms of mass percentage than any one of said additional, fractions the process further including separating $C_5$— and higher hydrocarbons produced by the butene methathesis from the reaction product and then converting the separated $C_5$— and higher hydrocarbons to propylene by recycling them and contacting them, together with the feedstock, with the transition metal oxide catalyst.

15. A process as claimed in claim 2, in which the reaction conditions include a temperature of 500–600° C.

16. A process for the production of propylene by butene metathesis which includes contacting a feedstock, which contains butene selected from the group consisting of 1-butene, 2-butene and mixtures thereof wherein the butene in the feedstock consists essentially of the butene selected from the group, with a catalyst which includes a catalytic amount of at least one metal oxide selected from the group consisting of the oxides of the transition metals, under reaction conditions which include a temperature of 500–600° C. and a pressure of 1–20 atmospheres, to convert the butene to propylene, thereby to produce a reaction product comprising a propylene fraction and, additional thereto, an ethylene fraction, a $C_4$ fraction and a $C_5$— and higher fraction, the propylene fraction being present in the reaction product in a higher proportion in terms of mass percentage than any one of said additional fractions.

17. A process for the production of propylene by butene metathesis which includes contacting a feedstock, which contains butene selected from the group consisting of 1-butene, 2-butene and mixtures thereof wherein the butene in the feedstock consists essentially of the butene from the group, with a catalyst which includes a catalytic amount of at least one metal oxide selected from the group consisting of the oxides of the transition metals, under reaction conditions which include a temperature of 500–600° C. and a pressure of 1–20 atmospheres, to convert the butene to a product comprising a higher percentage yield of propylene than of the percentage yields respectively of ethylene, $C_4$ hydrocarbons and $C_5$— and higher hydrocarbons.

* * * * *